United States Patent [19]

Shillington

[11] Patent Number: 5,862,530

[45] Date of Patent: Jan. 26, 1999

[54] PROTECTIVE EYEWEAR WITH FRAME AND DETACHABLE LENS

[76] Inventor: Richard A. Shillington, 5955 Lake Vista Dr., Bonsall, Calif. 92003-6104

[21] Appl. No.: 972,777

[22] Filed: Nov. 18, 1997

[51] Int. Cl.$^6$ .................................................. A61F 9/02
[52] U.S. Cl. ........................ 2/439; 2/450; 2/427; 351/92
[58] Field of Search ................................ 2/426, 427, 429, 2/430, 431, 432, 438, 439, 441, 442, 443, 445, 448, 449, 450, 451; 351/44, 41, 47, 92, 90, 91

[56] References Cited

U.S. PATENT DOCUMENTS

| | | | |
|---|---|---|---|
| D. 196,000 | 8/1963 | McNeil | D57/1 |
| D. 323,333 | 1/1992 | Jannard et al. | D16/112 |
| D. 347,017 | 5/1994 | Bolle | D16/112 |
| 2,423,539 | 7/1947 | Williams | 88/41 |
| 4,867,550 | 9/1989 | Jannard | 351/47 |
| 4,951,322 | 8/1990 | Lin | 2/439 |
| 4,972,521 | 11/1990 | Lison | 2/9 |
| 5,054,903 | 10/1991 | Jannard et al. | 351/123 |
| 5,137,343 | 8/1992 | Kelch et al. | 351/169 |
| 5,208,614 | 5/1993 | Jannard | 351/41 |
| 5,297,298 | 3/1994 | Salatka et al. | 2/447 |
| 5,357,292 | 10/1994 | Wiedner | 351/105 |
| 5,379,463 | 1/1995 | Schleger et al. | 2/431 |
| 5,379,464 | 1/1995 | Schleger et al. | 2/431 |
| 5,423,092 | 6/1995 | Kawai | 2/441 |

*Primary Examiner*—Michael A. Neas
*Assistant Examiner*—Larry D. Worrell, Jr.
*Attorney, Agent, or Firm*—Lyon & Lyon LLP

[57] ABSTRACT

Protective eyewear is described which includes a frame and a detachable lens. The frame has right and left temple flaps, each with at least one hole for locking the flaps onto corresponding detents molded into the temples of the frame. The lens may be molded in a ready-to-wear shape including temple portions, or it may be a flat shape for easy packaging. For the flat lens, a wearer can bend the lens appropriately to create the temple portions, thus forming a ready-to-wear shape. The lens is then secured to the frame by closing the flaps, thus sandwiching the temple portions of the lens between the flaps and the temples of the frame.

17 Claims, 5 Drawing Sheets

PROTECTIVE EYEWEAR WITH FRAME AND DETACHABLE LENS

FIELD OF THE INVENTION

The present invention relates to protective eyewear.

BACKGROUND OF THE INVENTION

Protective eyewear has many uses. For example, athletes often wear protective eyewear while participating in sports. Doctors, dentists, and their assistants often wear protective eyewear while performing medical or dental procedures. Many industrial personnel also wear protective eyewear to guard the eyes and face from flying debris. And recreational swimmers wear protective eyewear to help keep water out of the eyes.

Protective eyewear is currently available in various styles that generally include at least one or more lenses for the wearer to see through, and a frame to hold the lens or lenses in place. Many methods of attaching the lens or lenses to the frame exist, some methods having certain advantages over others. The lenses, however, are preformed into their ultimate shape, and are usually fixed to the frame. Lenses that are detachable from the frame are generally not very secure when in place, and may be difficult to re-attach or replace once they have been removed from the frame.

SUMMARY OF THE INVENTION

As used in this application, "temple" of the lens or of the frame refers to the general area of the lens or of the frame that would contact a wearer's temple, or rest within the general area of the wearer's temple, when the protective eyewear is properly worn. Thus, "temple" is not to be limited to any specific dimensions or artificial boundaries depending on the size of a particular wearer's head, particularly since the wearer's temple has no definite boundaries. Instead, "temple" is used regarding the lens to distinguish, for example, a certain portion of the lens from that portion of the lens covering the front of the eyes or the front of the face, or extending down the sides of the face. Regarding the frame, "temple" is used merely to distinguish a certain portion of the frame from, for example, a visor portion which extends generally out over the forehead, or the temple extensions which extend back from the temples of the frame and wrap around to the back of the wearer's head.

In a preferred embodiment, the present invention includes a frame and a single-piece detachable lens. The frame has right and left temple flaps, each with at least one hole for locking the flaps onto corresponding detents molded into the temples of the frame. The lens may be molded in a ready-to-wear shape including temple portions, or it may be manufactured in a flat shape for easy packaging and storage. The flat lens is made of a flexible material such as mylar, so the wearer can bend the lens appropriately to create the temple portions, forming substantially the ready-to-wear shape. In either case, at the temple portions of the lens, there are either holes to match corresponding detents in the frame, or detents to match corresponding holes in the frame. The temple portions of the lens are then secured to the frame by closing the flaps. This sandwiches the temple portions of the lens between the flaps and the temples of the frame, and locks the lens onto the frame by the hole-detent or detent-hole combination just described. This provides an easy attachment and detachment mechanism, and at the same time provides a secure attachment. The frame has flexible temple extensions that wrap around to the back of the wearer's head, and help secure the protective eyewear to the wearer's head by applying pressure to the back, temples, and sides of the head.

Thus, an object of the present invention is to provide improved protective eyewear.

Another object is to provide protective eyewear with a frame and a detachable lens, with an improved method of attachment of the protective eyewear to the lens.

Another object is to provide protective eyewear with a frame and a detachable lens, such that the lens may be disposed of and replaced as needed, without replacing the frame.

Another object is to provide protective eyewear with a detachable lens that may be secured to a frame by temple flaps molded into the frame.

Another object is to provide protective eyewear that may be manufactured, shipped, and stored in a substantially flat shape, and prior to use may be bent and attached to a frame.

Other objects and advantages of the present invention will become apparent from the detailed description of preferred embodiments which follow.

DETAILED DESCRIPTION

While the perspective views shown in the Figures result in more detail being visible on one side than on the other, it is to be understood that the side where the detail is not visible is preferably the same as the side where the detail is visible.

Figure 1:
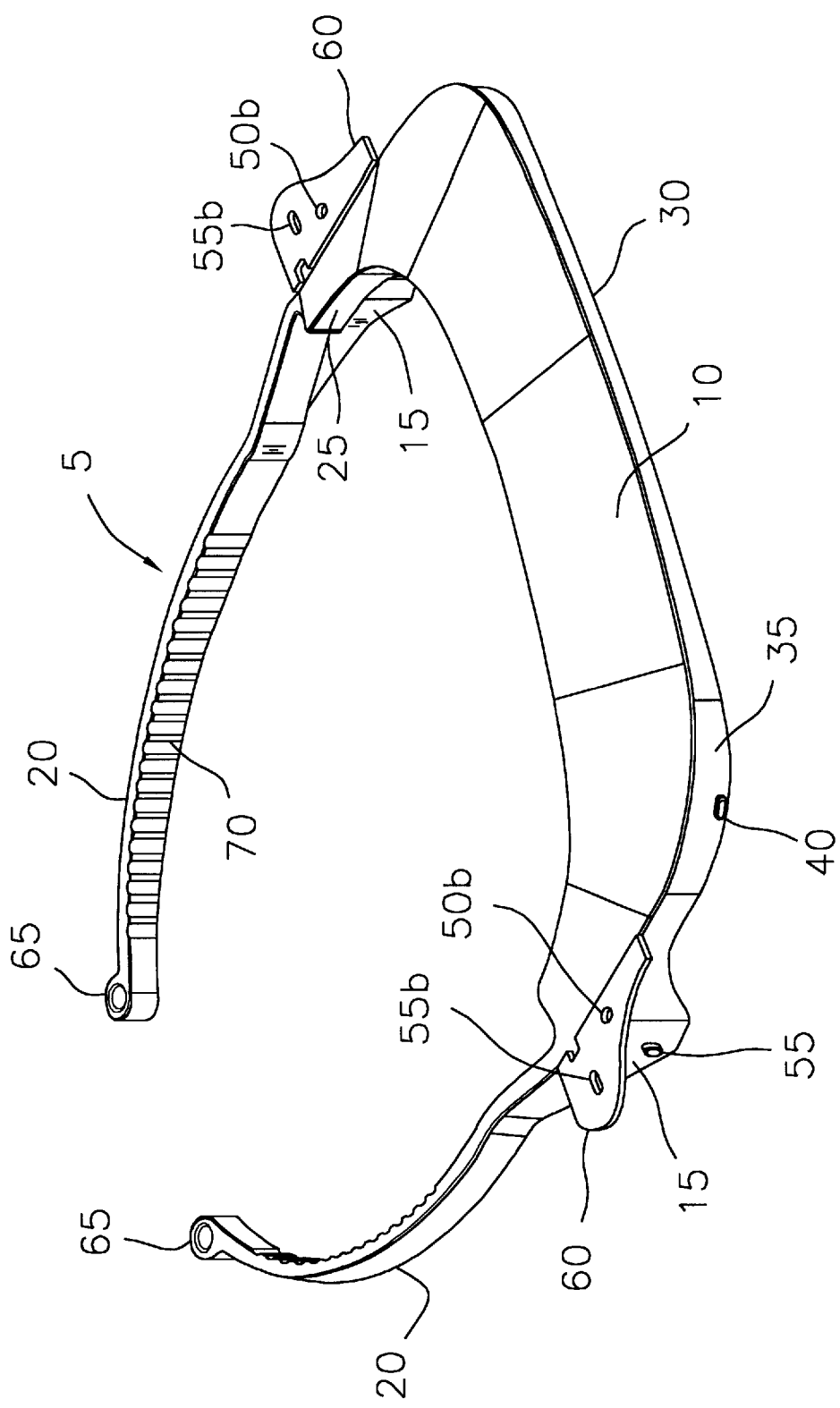
FIG. 1 is a perspective view of a preferred embodiment of the frame of the present invention, showing the temple flaps in an open position.

Turning to FIG. 1, a preferred embodiment of the frame 5 of the present invention is shown. The frame 5 is molded preferably from polypropylene or nylon, but may be molded from polyethylene or any plastic, so long as it is sturdy, yet flexible enough to fit various head sizes. The frame 5 may also be molded in various sizes, each size fitting a range of head sizes. The frame 5 has a visor 10 which extends generally from the wearer's temples out away from the wearer's forehead, temples 15 which rest within the general area of the wearer's temples when the protective eyewear is properly worn, and temple extensions 20 which extend back from the temples 15 of the frame 5 and wrap around to the back of the wearer's head.

The visor 10 has a back surface 25 which may contact the wearer's forehead. The visor 10 may extend outward from the wearer's forehead at its farthest point approximately one inch, one and a half inches, two inches, two and a half inches, or three inches, or between one and three inches, and terminates at a front surface 30 which has a downwardly extending rim 35. Detents 40 are molded into the rim 35 at appropriate locations to receive corresponding holes 40a in the lens 45 (see FIG. 2), thus helping secure the lens 45 to the frame 5. The lens 45 is also secured to the frame 5 by additional parts as will be described below.

As the visor 10 wraps around the wearer's forehead towards the back of the wearer's head, the visor 10 terminates approximately where the frame 5 would contact the wearer's temples. These portions of the frame 5 are referred to herein as the temples 15. Each temple 15 has molded detents 55 which correspond to holes 55b in temple flaps 60, which are also molded into the frame 5. The flaps 60 are molded as part of the frame, and are hingedly (as by a living hinge) attached to the front surface 30 of the visor 10. When the flaps 60 are open, as seen in FIGS. 1, 2, 4, and 5, they extend outward from the wearer's temples. The flaps 60 can be closed as seen in FIG. 3 by rotating them approximately ninety degrees toward the wearer's temples, placing the holes 55b over the corresponding detents 55. Closing the flaps 60 secures the lens 45 to the frame 5, as seen in FIG. 3, and as will be explained below. The shape of the flaps 60 preferably matches roughly the shape of the temples 15 of the frame 5, so the flaps 60 appear unobjectionable when closed.

As the frame 5 continues to wrap around the wearer's forehead from the visor 10 and past the temples 15 towards the back of the wearer's head, temple extensions 20 extend back from the temples 15. The temple extensions 20 wrap around to the back of the wearer's head, and may connect to each other at a central point in back of the wearer's head. Preferably, however, each temple extension 20 terminates near the back of the wearer's head, as seen in the Figures, such that the temple extensions 20 can be independently bent away from the wearer's head to allow the frame 5 to fit heads of various sizes. Where each temple extension 20 terminates, there is preferably a hole 65 molded into the extension 20 such that a string or other tightening mechanism may be used to tighten the extensions 20 around the wearer's head. The extensions 20 also preferably have anti-slip ridges 70 molded into them on the inner surface which may contact the wearer's head.

Figure 2:
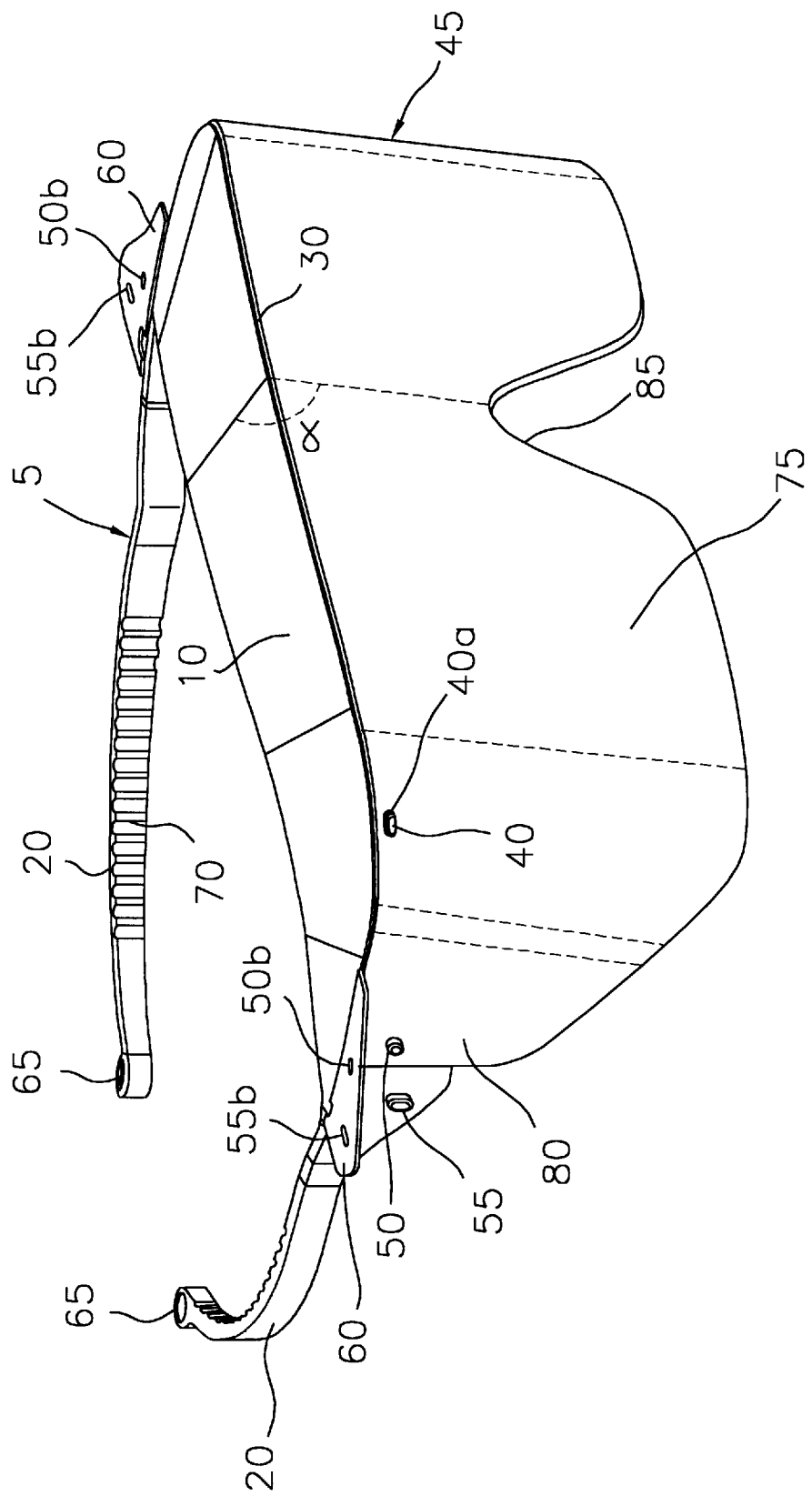
FIG. 2 is a perspective view of the frame in FIG. 1, with a preferred embodiment of the lens of the present invention attached, but not yet secured, to the frame, as the temple flaps are in an open position.
Figure 3:
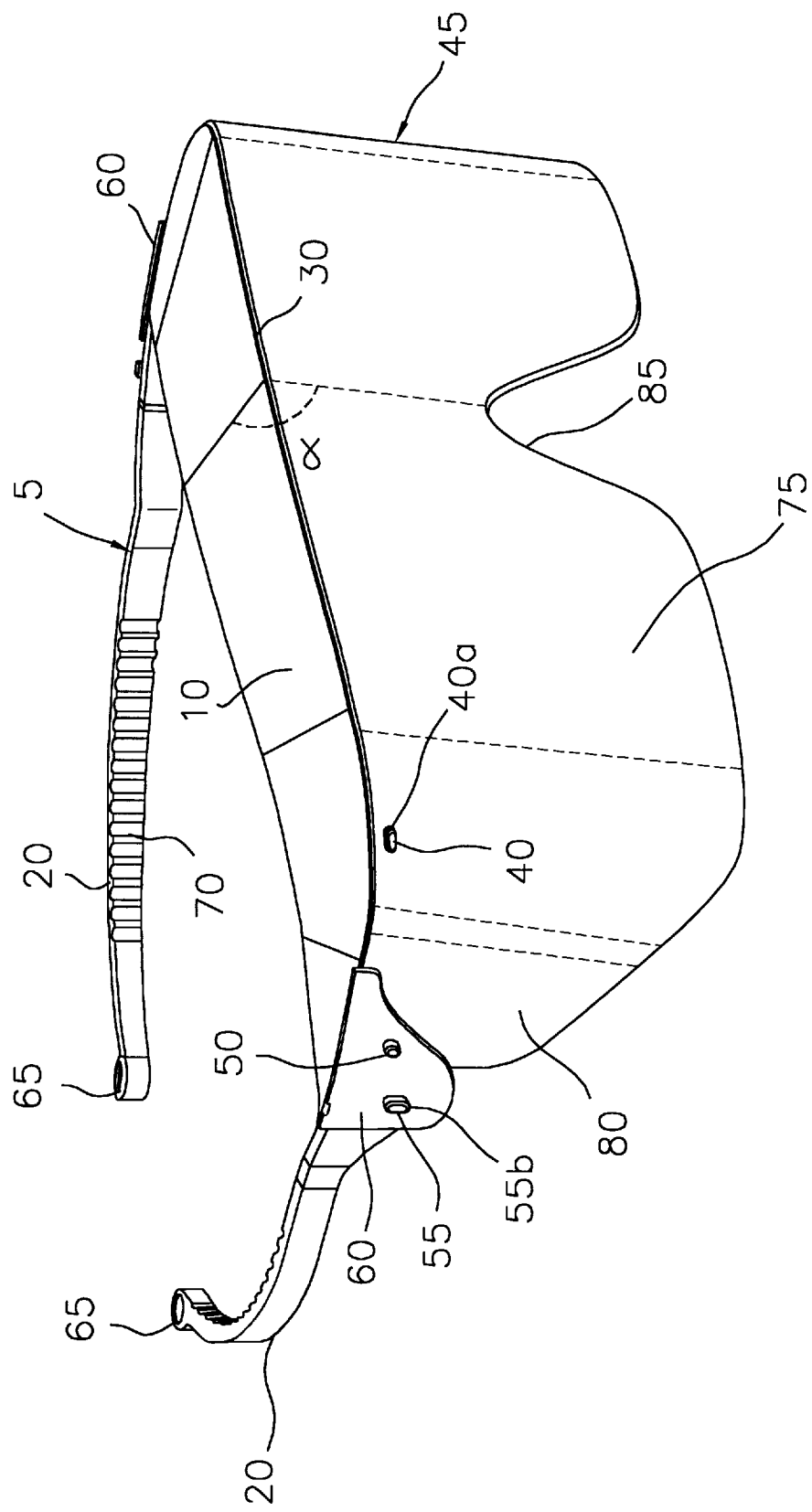
FIG. 3 is a perspective view of the frame and lens of FIG. 2, with the temple flaps in a closed position.

Turning now to FIG. 2, a preferred embodiment of the frame 5 and lens 45 of the present invention is shown, with the lens 45 attached to the frame 5 but not yet secured to the frame 5, as the temple flaps 60 are in an open position. The lens 45 in FIG. 2 is preferably rigid and formed by injection molded plastic or other material well-known in the art. The lens 45 may also provide protection from ultra-violet rays as is well known in the art. The lens 45 has a front portion 75 which covers a portion of the wearer's face, including at least the eyes, and temples 80 which wrap around to the wearer's temples. Peripheral vision is not disturbed by the temples 80 because the lens 45 is a single-piece lens. Detents 50 are molded into the temples 80 of the lens 45, and correspond to holes 50b in the temple flaps 60.

The front portion 75 of the lens 45 is preferably substantially flat, and therefore does not have any significant horizontal or vertical arcuate configuration. The front portion 75 extends downward from the rim 35 of the visor 10 at an angle α (see FIGS. 2–4), where a is preferably between eighty degrees and one hundred degrees. The best angle is approximately eighty five degrees. As previously described, the visor 10 extends outward from the wearer's forehead, thus when the frame 5 extends downward as just described, there is breathing space between the wearer's face and the lens 45. This configuration allows the wearer to use the protective eyewear of the present invention in conjunction with regular eyeglasses as the lens 45 is far enough away from the wearer's face so as not to interfere with the wearer's eyeglasses.

Figure 4:
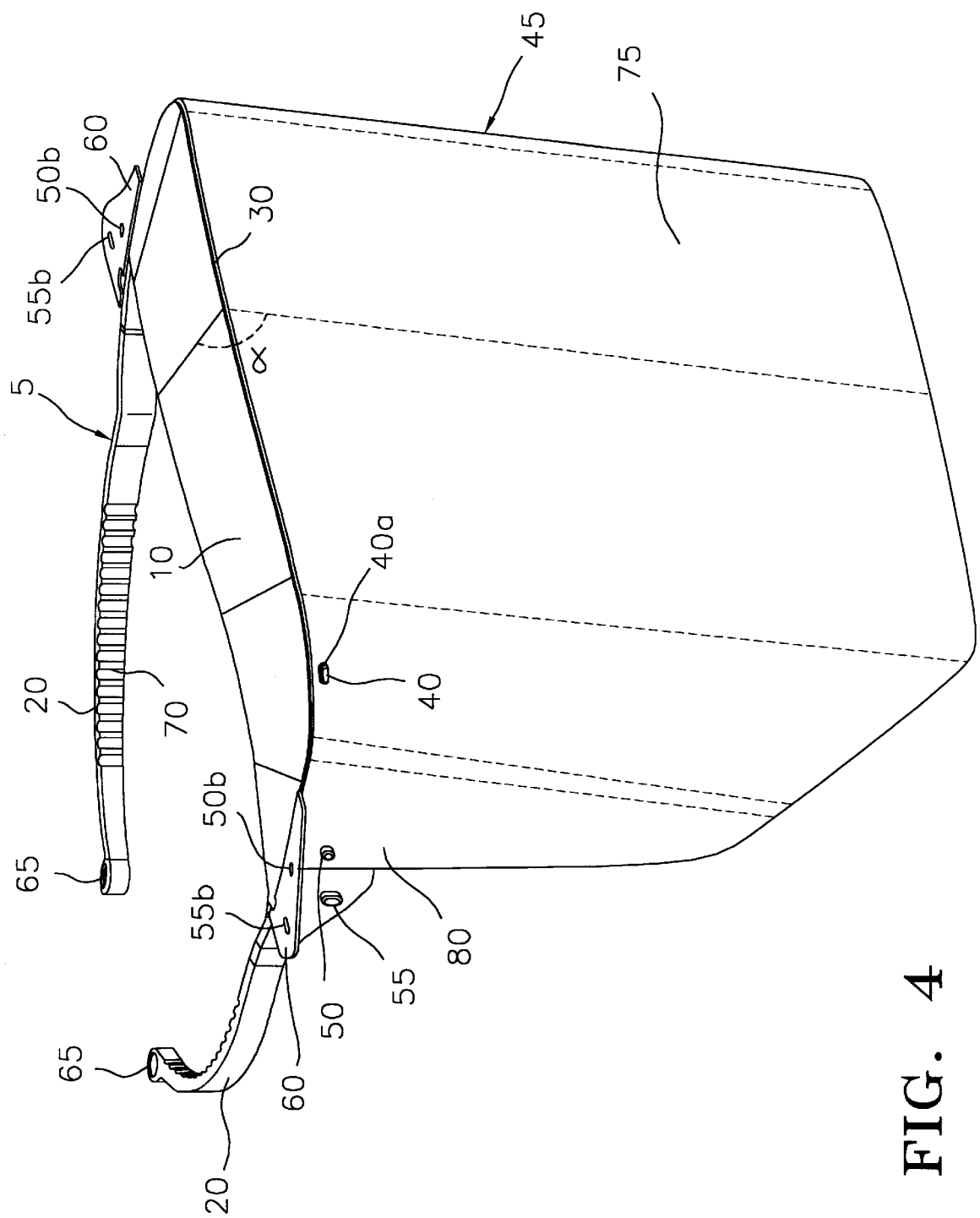
FIG. 4 is a perspective view of another preferred embodiment of the frame and lens of the present invention, showing the lens extending down to cover substantially the wearer's entire face.

The rigid lens 45 in FIG. 2 resembles conventional goggles, in that there is a nose bridge 85 which may rest on a wearer's nose. However, such a nose bridge 85 is not required, as the protective eyewear of the present invention relies on the temple extensions 20 for maintaining a secure fit of the protective eyewear to the wearer's head. Thus, the front portion 75 of the lens 45 could take on various shapes, so long as the lens 45 is adapted to be removably attached to the frame 5 as described below. For example, since the lens 45 does not rely on the nose bridge 85 for support, the lens 45 may extend down past the wearer's chin and act as a complete face shield, as seen in FIG. 4. The wearer may use the protective eyewear of the present invention, as in FIG. 4, while wearing a typical surgical mask, as the lens 45 is far enough away from the wearer's face due to the visor 10 so as not to interfere with the wearer's surgical mask. As another example (not shown), the lens 45 can have a front portion 75 which extends down as shown in FIG. 4, but temples 80 which extend down only as far as shown in FIG. 2.

The rigid lens 45 of FIG. 2 is attached to the frame 5 as shown in FIG. 3. The temple flaps 60 of the frame 5 must be opened as shown in FIG. 1. The lens 45 is then placed in position with the holes 40a fitting over the corresponding detents 40 on the rim 35 of the frame 5. The holes 40a are at locations between the front portion 75 and the right and left temples 80 approximately where the front portion 75 merges into the right and left temples 80. This configuration is best seen in FIG. 2. Once the lens 45 is in place, the temple flaps 60 are closed by rotating them approximately ninety degrees down toward the wearer's temples, placing the holes 50b and 55b over the corresponding detents 50 and 55 in the lens 45 and frame 5 respectively. Closing the flaps 60 secures the lens 45 in place by sandwiching the temple portions 80 of the lens 45 between the flaps 60 and the temples 15 of the frame 5, as seen in FIG. 3. In addition to the flaps 60, the detents 40 molded into the rim 35 of the frame 5 receive corresponding holes 40a in the lens 45, to help secure the lens 45 to the frame 5.

Figure 5:
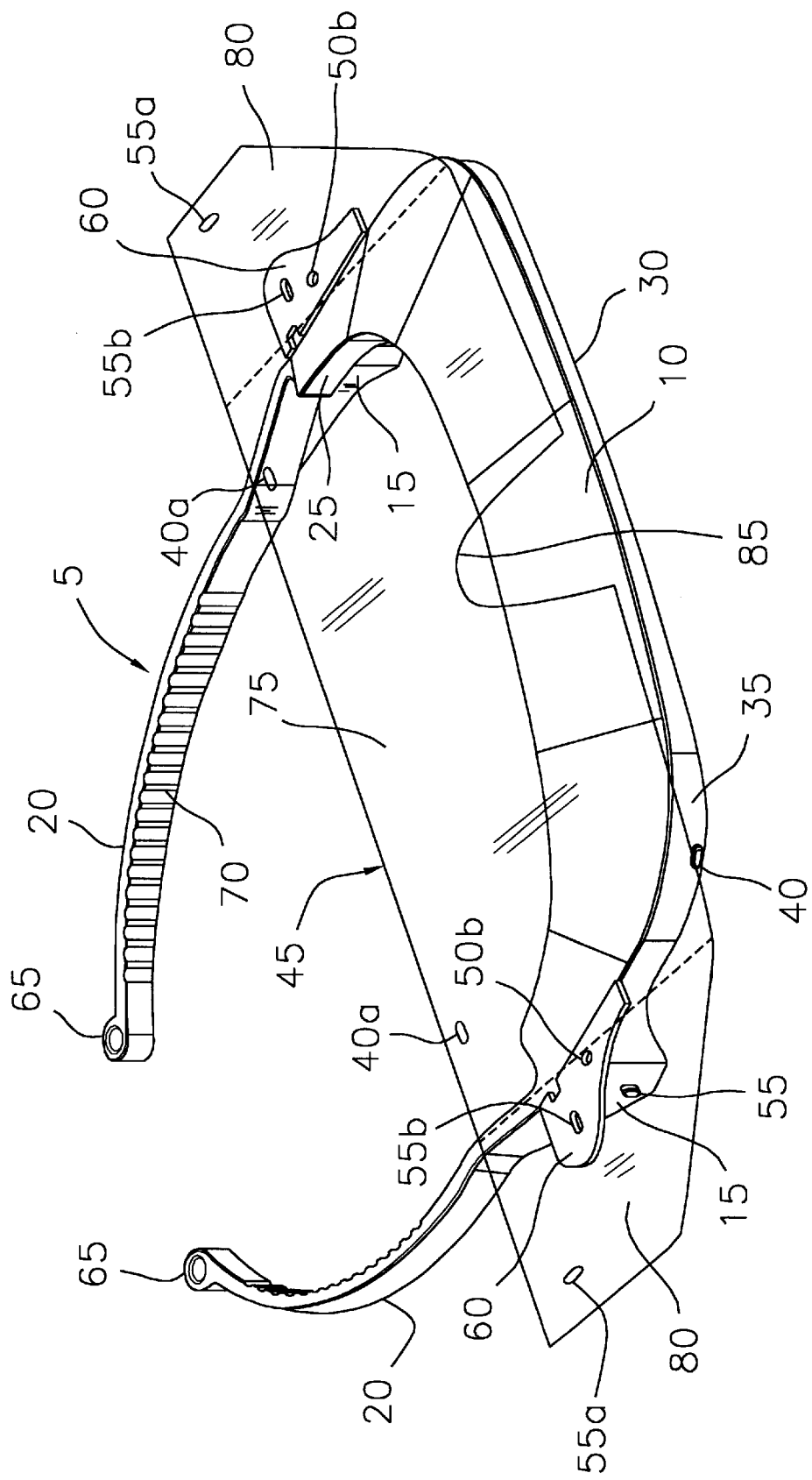
FIG. 5 is a perspective view of another preferred embodiment of the frame and lens of the present invention, showing the flexible lens molded in a flat shape for easy packaging.

If the lens 45 is the flat flexible lens as in FIG. 5, the lens 45 has holes 55a, instead of detents 50, at temples 80. To attach the flexible lens 45 to the frame 5, the lens 45 is bent at appropriate locations to create the temple portions 80, forming the lens 45 into a ready-to-wear shape. The lens 45 is then placed in position with the holes 40a fitting over the corresponding detents 40 on the rim 35 of the frame 5, as with the rigid lens 45. Once the lens 45 is in place, the temple flaps 60 are closed as previously described. But with the flexible lens 45, there are no detents 50 for the holes Sob of the flaps 60 to mate with. Instead, detents 55 on the frame 5 receive holes 55a of the lens 45, prior to receiving holes 55b of the flaps 60. Closing the flaps 60 thus sandwiches the temple portions 80 of the lens 45 between the flaps 60 and the temples 15 of the frame 5, just as with the rigid lens in FIG. 3. Preferably, after use the flexible lens 45 can be bent back to a substantially flat shape if desirable, and then bent back to a ready-to-wear shape for the next use. If the particular lens 45 is for a single use only, or if the lens 45 eventually wears out, the lens 45 could be disposed of and replaced by a new lens 45. The new lens 45 could then preferably be used with the old frame 5.

While certain embodiments are illustrated in the drawings and have just been described herein, it will be apparent to those skilled in the art that many modifications can be made to the embodiments without departing from the inventive concepts described. For example, the rigid lens 45 may have holes 55a in place of or in addition to detents 50, for attaching the lens 45 to the frame 5. Accordingly, the invention is not to be restricted except by the claims which follow.

What is claimed is:

1. A frame for use with a lens wherein the frame and the lens form protective eyewear for a wearer, the frame comprising:

a visor with a front surface that extends away from the head of the wearer and a back surface that rests substantially against the forehead of the wearer;

right and left temples that extend back from the visor toward the back of the wearer's head, the right and left temples both having an outwardly extending detent;

right and left temple extensions that extend back from the right and left temples respectively and wrap around to the back of the wearer's head; and right and left temple flaps hingedly attached to the front surface of the visor near the right and left temples respectively, the right and left temple flaps each comprising a first hole corresponding to the outwardly extending detents of the right and left temples respectively such that when the temple flaps are closed the outwardly extending detents extend through the respective first holes.

2. The frame as in claim 1 wherein the right and left temple flaps each have a second hole.

3. The frame as in claim 2 further comprising a rim that extends downward from the front surface of the visor and has at least two detents.

4. The frame as in claim 1 further comprising a rim that extends downward from the front surface of the visor and has at least two detents.

5. Protective eyewear for a wearer comprising:
a frame;
a single-piece lens removably attached to the frame;
wherein the frame comprises: a visor with a front surface which extends away from the head of the wearer and a back surface which rests substantially against the forehead of the wearer; right and left temples which extend back from the visor toward the back of the wearer's head; and right and left temple extensions which extend back from the right and left temples respectively and wrap around to the back of the wearer's head;
wherein the frame further comprises an outwardly extending detent on each of the right and left temples;
wherein the frame further comprises right and left temple flaps hingedly attached to the front surface of the visor near the right and left temples respectively, and the right and left temple flaps each comprise a first hole corresponding to the outwardly extending detents of the right and left temples respectively such that when the temple flaps are closed the outwardly extending detents extend through the respective first holes;
wherein the single-piece lens has a front portion which covers a portion of the wearer's face, including at least the eyes, and temples which wrap around to the wearer's temples;
wherein the single-piece lens further comprises right and left detents on the right and left temples of the lens respectively; and
wherein the right and left temple flaps each further comprise a second hole corresponding to the detents on the temples of the lens such that when the temple flaps are closed the detents on the temples of the lens extend through the respective second holes.

6. The protective eyewear as in claim 5 wherein the frame further comprises at least two detents positioned on the rim of the front surface of the visor, and the lens further comprises corresponding holes which fit over the at least two detents.

7. The protective eyewear as in claim 6 wherein the front of the lens extends downward to cover substantially the entire front of the wearer's face.

8. The protective eyewear as in claim 5 wherein the front of the lens extends downward to cover substantially the entire front of the wearer's face.

9. The protective eyewear as in claim 8 wherein the visor extends out away from the wearer's forehead at its farthest point by at least approximately two inches.

10. The protective eyewear as in claim 5 wherein the visor extends out away from the wearer's forehead at its farthest point by at least approximately two inches.

11. Protective eyewear for a wearer comprising:
a frame comprising a visor with a front surface which extends away from the head of the wearer and a back surface which rests substantially against the forehead of the wearer; right and left temples which extend back from the visor toward the back of the wearer's head; right and left temple extensions which extend back from the right and left temples respectively and wrap around to the back of the wearer's head; an outwardly extending detent on each of the right and left temples; right and left temple flaps hingedly attached to the front surface of the visor near the right and left temples respectively, and the right and left temple flaps each have a first hole corresponding to the outwardly extending detents of the right and left temples respectively such that when the temple flaps are closed the outwardly extending detents extend through the respective first holes;
a lens removably attached to the frame having a front portion that covers a portion of the wearer's face, including at least the eyes, and right and left temples that wrap around to the wearer's temples and each have a hole corresponding to the outwardly extending detents of the right and left temples of the frame respectively; and
the right and left temple flaps each having a second hole corresponding to the detents on the temples of the lens such that when the temple flaps are closed the detents on the temples of the lens extend through the respective second holes.

12. The protective eyewear as in claim 11 wherein the frame further comprises at least two detents positioned on the rim of the front surface of the visor, and the lens further comprises corresponding holes which fit over the at least two detents.

13. The protective eyewear as in claim 12 wherein the front of the lens extends downward to cover substantially the entire front of the wearer's face.

14. The protective eyewear as in claim 11 wherein the front of the lens extends downward to cover substantially the entire front of the wearer's face.

15. The protective eyewear as in claim 14 wherein the visor extends out away from the wearer's forehead at its farthest point by at least approximately two inches.

16. The protective eyewear as in claim 11 wherein the visor extends out away from the wearer's forehead at its farthest point by at least approximately two inches.

17. The protective eyewear as in claim 11 wherein the lens is a flexible material such that it can be stored in a substantially flat position and be bent into an appropriate shape to cooperate with the frame when ready for use as the protective eyewear.

* * * * *

UNITED STATES PATENT AND TRADEMARK OFFICE
CERTIFICATE OF CORRECTION

PATENT NO. : 5,862,530
DATED : January 26, 1999
INVENTOR(S) : Richard A. Shillington

It is certified that error appears in the above-identified patent and that said Letters Patent is hereby corrected as shown below:

Column 3, line 61, after where, change "a" to " -- $\alpha$ --.

Column 4, line 49, change "Sob" to -- 50b --.

Signed and Sealed this

Twenty-second Day of May, 2001

Attest:

NICHOLAS P. GODICI

*Attesting Officer*   *Acting Director of the United States Patent and Trademark Office*